United States Patent
Ban et al.

(10) Patent No.: US 11,044,684 B2
(45) Date of Patent: *Jun. 22, 2021

(54) METHOD AND DEVICE FOR MEASURING AMOUNT OF USER PHYSICAL ACTIVITY

(71) Applicant: Samsung Electronics Co., Ltd., Suwon-si (KR)

(72) Inventors: Ji-Hye Ban, Suwon-si (KR); Sun-Mi Park, Seoul (KR); Jeong-Min Park, Suwon-si (KR); Dae-Yong Lee, Suwon-si (KR); Youn-Hee Lee, Seoul (KR); Jae-Woong Chun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,329

(22) Filed: Dec. 8, 2017

(65) Prior Publication Data

US 2018/0110021 A1 Apr. 19, 2018

Related U.S. Application Data

(63) Continuation of application No. 14/678,379, filed on Apr. 3, 2015, now Pat. No. 9,867,152.

(30) Foreign Application Priority Data

Apr. 4, 2014 (KR) .................. 10-2014-0040606

(51) Int. Cl.
*H04W 56/00* (2009.01)
*A61B 5/11* (2006.01)
(Continued)

(52) U.S. Cl.
CPC .......... *H04W 56/001* (2013.01); *A61B 5/002* (2013.01); *A61B 5/1118* (2013.01); *H04W 4/80* (2018.02);
(Continued)

(58) Field of Classification Search
CPC .... H04W 56/001; H04W 4/008; A61B 5/002; A61B 5/1118; A61B 5/6803; A61B 5/681;
(Continued)

(56) References Cited

U.S. PATENT DOCUMENTS 6,571,193 B1 5/2003 Unuma et al.
6,584,439 B1 6/2003 Geilhufe et al.
(Continued)

FOREIGN PATENT DOCUMENTS

KR 10-2010-0023388 A 3/2010
KR 10-2010-0025382 A 3/2010
KR 10-2012-0098854 A 9/2012

*Primary Examiner* — Gennadiy Tsvey
(74) *Attorney, Agent, or Firm* — Jefferson IP Law, LLP

(57) ABSTRACT

An electronic device and a method of measuring an amount of user physical activity by an electronic device are provided. The method includes establishing short range communication among a plurality of electronic devices, determining one of the plurality of electronic devices as a primary device, communicating state information of remaining electronic devices to the primary device, activating a sensor on a device having a highest priority among the plurality of electronic devices according to the state information, recording physical activity information according to physical activity sensed by the sensor, communicating the physical activity information to the primary device, calculating an amount of physical activity according to the communicated physical activity information, and synchronizing the amount of physical activity among the plurality of electronic devices.

14 Claims, 8 Drawing Sheets

(51) Int. Cl.
*H04W 4/80* (2018.01)
*A61B 5/00* (2006.01)

(52) U.S. Cl.
CPC .............. *A61B 5/0004* (2013.01); *A61B 5/112* (2013.01); *A61B 5/681* (2013.01); *A61B 5/6803* (2013.01); *A61B 5/6807* (2013.01); *A61B 5/7246* (2013.01); *A61B 2560/0475* (2013.01)

(58) Field of Classification Search
CPC ................ A61B 5/6807; A61B 5/7246; A61B 2560/0475; A61B 5/112; A61B 5/0004
See application file for complete search history.

(56) References Cited

U.S. PATENT DOCUMENTS

| | | |
|---|---|---|
| 8,446,275 B2 | 5/2013 | Utter, II |
| 8,745,247 B1 | 6/2014 | Park et al. |
| 10,352,724 B1* | 7/2019 | Dixit .................... G01C 22/006 |
| 2004/0094613 A1 | 5/2004 | Shiratori et al. |
| 2005/0248718 A1 | 11/2005 | Howell et al. |
| 2007/0060118 A1 | 3/2007 | Guyette |
| 2009/0191514 A1 | 7/2009 | Barnow |
| 2011/0275940 A1 | 11/2011 | Nims et al. |
| 2012/0203360 A1 | 8/2012 | Tagliabue |
| 2013/0151699 A1 | 6/2013 | Vock et al. |
| 2013/0325396 A1 | 12/2013 | Yuen et al. |
| 2013/0325404 A1 | 12/2013 | Yuen et al. |
| 2014/0031703 A1* | 1/2014 | Rayner .............. A61B 5/02055 600/484 |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0088922 A1 | 3/2014 | Messenger et al. |
| 2014/0089514 A1 | 3/2014 | Messenger et al. |
| 2014/0156228 A1 | 6/2014 | Molettiere et al. |
| 2014/0163927 A1 | 6/2014 | Molettiere et al. |
| 2014/0164611 A1 | 6/2014 | Molettiere et al. |

\* cited by examiner

METHOD AND DEVICE FOR MEASURING AMOUNT OF USER PHYSICAL ACTIVITY

CROSS-REFERENCE TO RELATED APPLICATION(S)

This application is a continuation application of prior application Ser. No. 14/678,379, filed on Apr. 3, 2015, which claimed the benefit under 35 U.S.C. § 119(a) of a Korean patent application filed on Apr. 4, 2014 in the Korean Intellectual Property Office and assigned Serial number 10-2014-0040606, the entire disclosure of which is hereby incorporated by reference.

TECHNICAL FIELD

The present disclosure relates to a method and a device for measuring an amount of user physical activity.

BACKGROUND

In general, a step counter is a representative device for measuring an amount of user physical activity. When a user moves, the step counter counts the number of footsteps of the user through a sensor while being worn on the user's body.

In recent years, the step counter is provided to a user in the form of being coupled to shoes or as a wearable wristband. Furthermore, electronic devices such as a watch, a mobile phone, and a smart phone may provide the step count function. Accordingly, multiple step counters may simultaneously operate while being worn on the user's body.

However, in reality it is difficult to wear the step counter on the user's body around the clock. Although a wearable device may be more frequently worn the user's body as compared with the smart phone, the wearable device is not often worn on the user's body on account of practical conditions such as battery charging.

Furthermore, in a case where a user wears a plurality of devices having similar step count functions on his/her body at the same time, the respective step counters may independently count steps of the user. However, since sensors provided to the respective step counters, or performances of the step counters, may be different from each other, the number of steps counted by the devices may also be different.

In addition, the step counters may be worn on the user's body in different time zones, and therefore it may also be difficult for this reason to finally calculate the amount of user physical activity.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method and a device which can exclude unnecessary repetitive measurement and prevent excessive or insufficient measurement for an amount of physical activity through efficient synchronization when there are two or more devices for measuring the amount of physical activity.

Another aspect of the present disclosure is to provide a method and a device which can reduce power consumption by controlling unnecessary measurement by step counters.

Another aspect of the present disclosure is to provide a method and a device which can effectively use a memory restricted by a low-power sensing platform of a wearable device, and are suitable to express the amount of physical activity from a heuristic perspective.

In accordance with one aspect of the present disclosure, a method of measuring an amount of user physical activity by an electronic device is provided. The method includes counting, by the electronic device and at least one other device, an amount of physical activity, storing, by the electronic device, first count information including a first count start time, a first count end time, and a first amount of physical activity counted between the first count start time and the first count end time, receiving, by the electronic device, second count information including a second count start time, a second count end time, and a second amount of physical activity from the at least one other device when the electronic device is connected with the at least one other device through short range communication, determining an integrated amount of physical activity using the first count information and the second count information, and changing an entire amount of physical activity corresponding to the electronic device according to the integrated amount of physical activity, transmitting the integrated amount of physical activity to the at least one other device, and performing synchronization between the electronic device and the at least one other device of the amount of physical activity.

In accordance with another aspect of the present disclosure, an electronic device is provided. The electronic device includes a sensor, and a measurement module configured to count an amount of physical activity using a sensor value of the sensor, to store count information including a first count start time, a first count end time, and a first amount of physical activity counted between the first count start time and the first count end time in a memory, to receive second count information including a second count start time, a second count end time, and a second amount of physical activity from at least one other device when the electronic device is connected with the at least one other device through short range communication, to determine an integrated amount of physical activity using the first count information and the second count information, to change an entire amount of physical activity corresponding to the electronic device according to the integrated amount of physical activity, to transmit the integrated amount of physical activity to the at least one other device, and to perform synchronization between the electronic device and the at least one other device of the amount of physical activity.

Another aspect of the present disclosure is to provide a method and a device which can exclude unnecessary repetitive measurement and prevent excessive or insufficient measurement for an amount of physical activity through efficient synchronization when there are two or more devices for measuring the amount of physical activity.

Another aspect of the present disclosure is to provide a method and a device which can reduce power consumption by controlling unnecessary measurement by step counters.

Another aspect of the present disclosure is to provide a method and a device which can effectively use a memory restricted by a low-power sensing platform of a wearable device and are suitable to express the amount of physical activity from a heuristic perspective.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
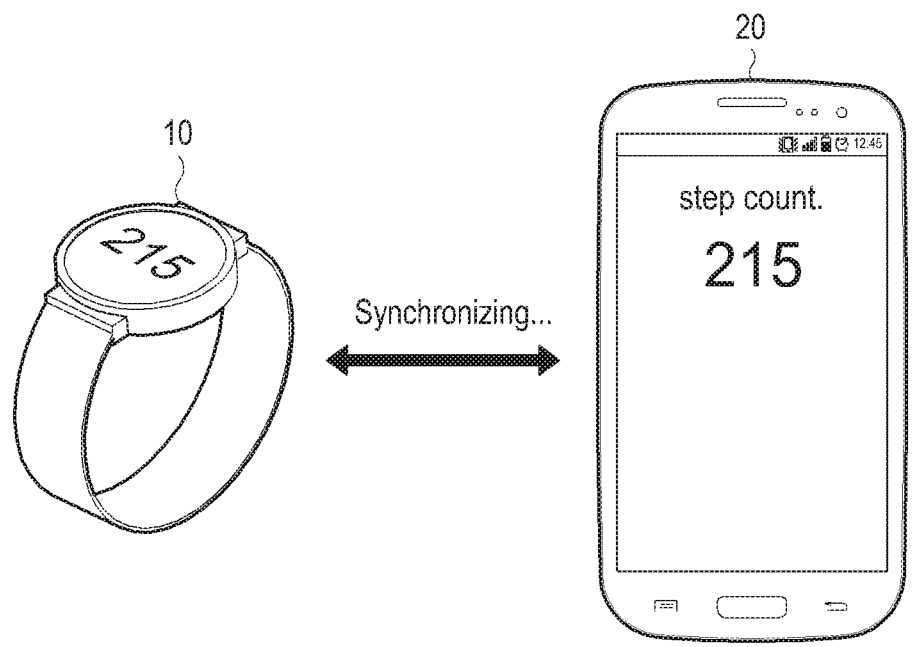
FIG. 1 illustrates a plurality of electronic devices for measuring the number of steps according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The expressions that may be used in various embodiments of the present disclosure, such as, "comprise", "may comprise" or the like indicate the existence of a disclosed corresponding function, operation, component element, or the like, and may not limit additional one or more functions, operations, component elements or the like. Further, as used in various embodiments of the present disclosure, the terms "include", "have" and their conjugates may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

The expression such as "or" or the like in various embodiments of the present disclosure include any and all of the combinations of words disclosed together. For example, the expression "A or B" may include A, may include B, or may include both A and B.

The expressions "1", "2", "first", or "second" used in various embodiments of the present disclosure may modify various components of various embodiments but does not limit the corresponding components. For example, the above expressions do not limit the sequence and/or importance of the corresponding constituent elements. The above expressions may be used merely to distinguish a constituent element from other constituent elements. For example, a first user device and a second user device indicate different user devices, although both of them are user devices. For example, without departing from the scope of the present disclosure, a first component element may be named a second component element. Similarly, the second component element also may be named the first component element.

It should be noted that if it is described that one component element is "coupled" or "connected" to another component element, the first component element may be directly coupled or connected to the second component, and a third component element may be "coupled" or "connected" between the first and second component elements. In contrast, when it is stated that a component is directly "coupled to" or "connected to" another component, a new component does not exist between the component and another component.

The terms used in various embodiments of the present disclosure are merely used to exemplify a certain embodiment and should not limit various embodiments of the present disclosure. As used herein, the singular forms are intended to include the plural forms as well, unless the context clearly indicates otherwise.

Unless defined differently, all terms used herein, which include technical terminologies or scientific terminologies, have the same meaning as a person skilled in the art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present disclosure.

An electronic device according to various embodiments of the present disclosure may be a device having a step counting function for measuring the number of steps. For example, the electronic device may include at least one of a smart phone, a tablet Personal Computer (PC), a mobile phone, a video phone, an electronic book reader (e-book reader), a desktop PC, a laptop PC, a netbook computer, a Personal Digital Assistant (PDA), a Portable Multimedia Player (PMP), a digital audio player, a mobile medical device, a camera, and a wearable device, for example, a Head-Mounted Device (HMD) such as electronic glasses, electronic clothes, an electronic bracelet, an electronic necklace, an electronic appcessory, an electronic tattoo, or a smart watch.

According to some embodiments, the electronic device may include at least one of various medical devices (e.g., Magnetic Resonance Angiography (MRA)), a navigation device, a Global Positioning System (GPS) receiver, an Event Data Recorder (EDR), a Flight Data Recorder (FDR), an automobile infotainment device, a security device, and a home robot.

Also, an electronic device according to various embodiments of the present disclosure may be a flexible device. Also, an electronic device according to various embodiments of the present disclosure is not limited to the above described devices.

Hereinafter, an electronic device according to various embodiments will be described with reference to the accompanying drawings. The term "user" used in various embodiments may indicate a user who uses an electronic device or a device that uses an electronic device such as an artificial intelligence electronic device.

According to various embodiments of the present disclosure, a plurality of electronic devices each having a function of measuring an amount of user physical activity, for example, a step count function of measuring the number of steps, are interworked with each other, thereby more efficiently measuring the number of steps.

FIG. 1 illustrates a plurality of electronic devices for measuring the number of steps according to an embodiment of the present disclosure.

An electronic watch 10 and a smart phone 20 which are illustrated in FIG. 1 each have a step count function and therefore, may individually count steps. However, count values of the two devices may be different from each other. Accordingly, in the various embodiments of the present disclosure, in order to provide a user with a measurement value for the integrated amount of physical activity, the step count values may be synchronized, thereby making it possible to ensure they display the same number of steps. According to an embodiment, the two devices 10 and 20 may be connected with each other through short range communication.

Referring to FIG. 1, among the plurality of devices having the function of measuring the amount of physical activity (e.g., the step count function), one device that collects count information on the amount of physical activity (e.g., the number of steps) to determine the integrated amount of the physical activity, and transfers the integrated amount of the physical activity to the other device to perform synchronization of the amount of physical activity, may be referred to as a main device. The other device may be referred to as a sub-device. The main device is not fixed, and among the plurality of devices connected through the short range communication, any device capable of calculating the integrated amount of the physical activity may be used as the main device.

Figure 2:
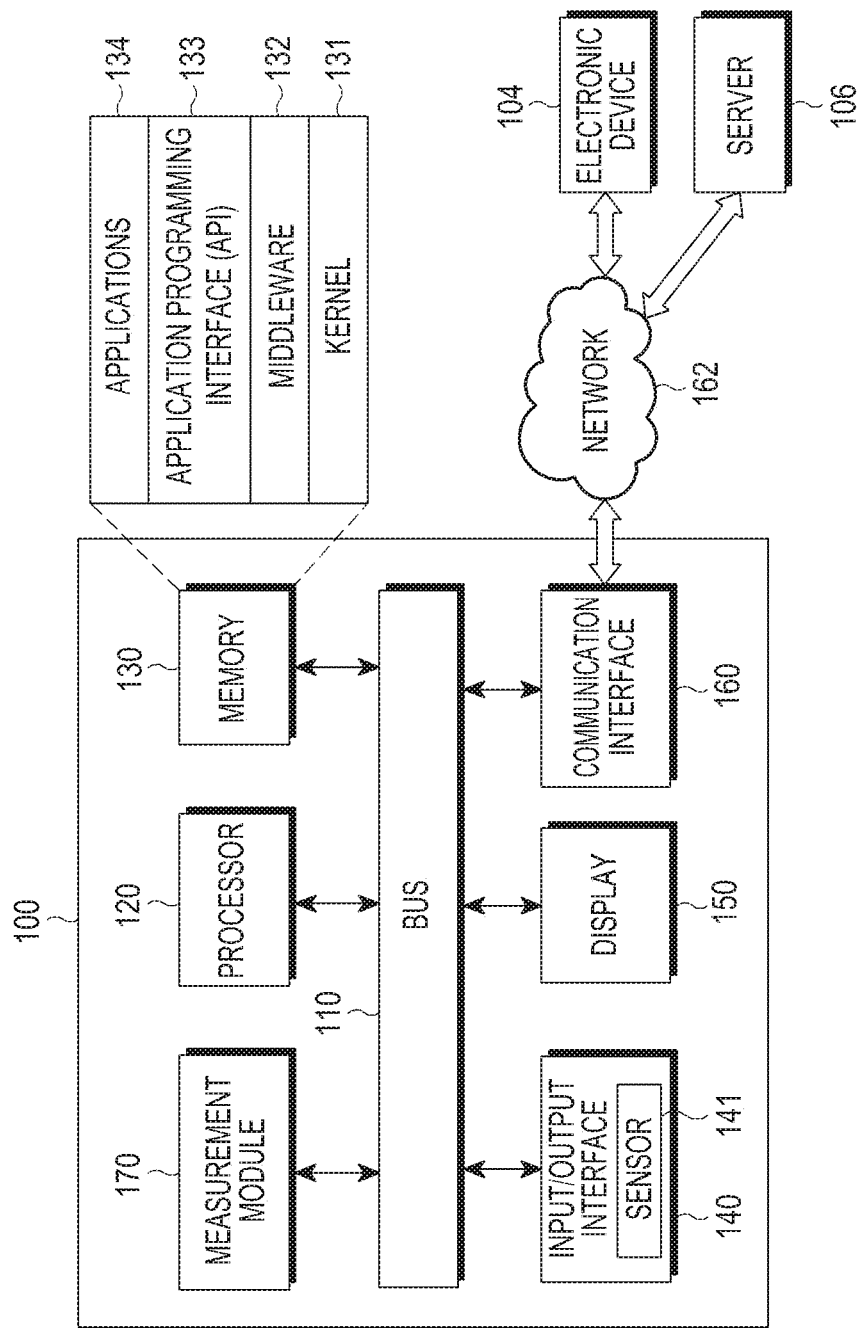
FIG. 2 is a block diagram illustrating a network environment including an electronic device according to an embodiment of the present disclosure.

FIG. 2 is a block diagram illustrating a network environment including an electronic device which may serve as a main device according to various embodiments of the present disclosure.

Referring to FIG. 2, an electronic device 100 may include a bus 110, a processor 120, a memory 130, an input/output interface 140, a communication interface 160, a sensor 141, and a measurement module 170. The electronic device 100 may further include a display 150.

The bus 110 may be a circuit connecting the aforementioned components and transmitting communication (for example, a control message) between the aforementioned components.

For example, the processor 120 may receive instructions from the aforementioned other elements (e.g., the memory 130, the input/output interface 140, the display 150, the communication interface 160, and the measurement module 170) through the bus 110, decipher the received instructions, and perform calculation or data processing according to the deciphered instructions.

The memory 130 may store instructions or data received from or created by the processor 120 or other elements (e.g., the input/output interface 140, the display 150, the communication interface 160, and the measurement module 170). The memory 130 may include programming modules, for example, a kernel 131, middleware 132, an Application Programming Interface (API) 133, and applications 134. Each of the programming modules described above may be configured by software, firmware, hardware, or combinations of two or more thereof.

The kernel 131 may control or manage system resources (for example, the bus 110, the processor 120, or the memory 130) used for executing an operation or function implemented in the other programming modules, for example, the middleware 132, the API 133, or the applications 134. Furthermore, the kernel 131 may provide an interface through which the middleware 132, the API 133, or the applications 134 may access individual components of the electronic device 100 to control or manage the components.

The middleware 132 may perform a relay function of allowing the API 133 or the applications 134 to communicate with the kernel 131 to exchange data. Furthermore, in regard to task requests received from the applications 134, the middleware 132 may perform a control (e.g., scheduling or load balancing) for the task requests using, for example, a method of assigning a priority for using the system resources (e.g., the bus 110, the processor 120, and the memory 130) of the electronic device 100 to at least one of the applications 134.

The API 133 is an interface through which the applications 134 may control functions provided by the kernel 131 and the middleware 132, and may include at least one interface or function (e.g., instruction) for file control, window control, image processing, or text control.

According to various embodiments, the applications 134 may include an Short Message Service (SMS)/Multimedia Messaging Service (MMS) application, an e-mail application, a calendar application, an alarm application, a health care application (e.g., an application for measuring an amount of exercise or blood sugar), and an environmental information application (e.g., an application for providing an atmospheric pressure, humidity, temperature, and the like). Additionally or alternately, the applications 134 may include an application related to an information exchange between the electronic device 100 and an external electronic device (e.g., an electronic device 104). The application associated with the information exchange may include, for example, a notification relay application for transferring specific information to the external electronic device or a device management application for managing the external electronic device.

For example, the notification relay application may include a function of transferring, to the external electronic device (e.g., the electronic device 104), notification information generated from other applications of the electronic device 100 (e.g., an SMS/MMS application, an e-mail application, a health management application, an environmental information application, and the like). Additionally or alternatively, the notification relay application may receive the notification information from, for example, the external electronic device (e.g., the electronic device 104), and may provide the received notification information to a user. The device management application may manage (for example, install, delete, or update), for example, a function of at least a part of the external electronic device (e.g., the electronic device 104) that communicates with the electronic device 100 (for example, activating/deactivating the external electronic device (or some component elements) or adjusting brightness (or resolution) of a display), an application operating in the external electronic device, or a service provided from the external electronic device (e.g., a call service or a message service).

According to various embodiments, the applications 134 may include an application designated based on an attribute (e.g., a type) of the external electronic device (e.g., the electronic device 104). For example, in a case where the external electronic device is an MP3 player, the applications 134 may include an application related to reproduction of music. Similarly, in a case where the external electronic device is a mobile medical appliance, the applications 134 may include an application related to health care. According to an embodiment, the applications 134 may include at least one of an application designated to the electronic device 100 and an application received from the external electronic device (e.g., a server 106 or the electronic device 104).

According to an embodiment, the applications 134 may include an application for measuring an amount of physical activity. The application for measuring the amount of physical activity is an application related to measurement for an amount of user physical activity, and may include, for example, a step count application and an application for measuring a heart rate.

According to embodiments, the memory 130 may store count information. The count information may include start time when a physical activity count is initiated, end time when the physical activity count is terminated, and an amount of physical activity measured between the start time and the end time. For example, in a case where the amount of physical activity corresponds to the number of steps, the count information may include a start time when a step count is initiated, an end time when the step count is terminated, and a number of steps measured between the start time and the end time. If the number of steps, namely, the amount of physical activity has not been continuously measured, a plurality of pieces of count information may be stored in the memory 130.

According to another embodiment, for various types of devices having the function of measuring the amount of physical activity, a priority depending on reliability of the devices for the measurement of the amount of physical activity may be stored in the memory 130. For example, in a case where the function of measuring the amount of physical activity is a step count function, for various types of devices having the step count function, a priority depending on reliability of the devices for a step count may be stored in the memory 130.

For example, in a smart watch and a smart phone, step detection of the smart watch worn on a user's body may be more reliable than that of the smart phone. Furthermore, in a smart watch and a step counter mounted to shoes, reliability of the step counter mounted to the shoes may be higher than that of the smart watch. Accordingly, in various types of devices, a priority depending on reliability of the devices for the step detection may be stored in the memory 130.

In addition, a priority may also be stored in the memory 130 in view of status information according to whether a wearable device having the function of measuring the amount of physical activity has been worn on a user's body. For example, the priority may be stored in the memory 130 in view of status information according to whether a wearable device having the step count function has been worn on a user's body.

The input/output interface 140 may transfer instructions or data input from a user through an input/output device (e.g., the sensor 141, a keyboard, or a touch screen) to, for example, the processor 120, the memory 130, the communication interface 160, or the measurement module 170 through the bus 110. For example, the input/output interface 140 may provide, to the processor 120, data for a user's touch input through a touch screen. Furthermore, through the input/output device (e.g., a speaker (not shown) or the display 150), the input/output interface 140 may output instructions or data received from the processor 120, the memory 130, the communication interface 160, or the measurement module 170 through the bus 110. For example, the input/output interface 140 may output voice data processed through the processor 120 to a user through the speaker.

The sensor 141 may include an accelerometer, a motion sensor such as a gyroscope based on an Inertial Navigation System (INS), and a gesture sensor. The sensor may sense a movement of a device to detect a user's movement such as walking, leaping, jumping, an uphill path, a downhill path, and stairs. Based on such a movement, an amount of physical activity such as the number of steps may be counted, and an amount of calorie expenditure may also be calculated through detection of the amount of physical activity.

In regard to a physical activity measuring device mounted to shoes, a pressure sensor based on pressure may be used as a sensor for determining walking. The pressure sensor may provide more detailed information related to a user's movement, by distinguishing situations such as running, walking, jumping, and the like through the measured pressure intensity.

The display 150 may display various pieces of information (e.g., multimedia data or text data) to a user.

The communication interface 160 may conduct communication between the electronic device 100 and the external electronic device (e.g., the electronic device 104 or the server 106). For example, the communication interface 160 may be connected to a network 162 through wireless or wired communication to communicate with the external device. The wireless communication may include at least one of, for example, WiFi, BLUETOOTH (BT), Near Field Communication (NFC), GPS and cellular communication (for Long Term Evolution (LTE), LTE-Advanced (LTE-A), Code Division Multiple Access (CDMA), Wideband CDMA (WCDMA), Universal Mobile Telecommunication System (UMTS), Wireless Broadband (WiBro), Global System for Mobile communication (GSM), and the like). The wired communication may include at least one of, for example, a Universal Serial Bus (USB), a High Definition Multimedia Interface (HDMI), Recommended Standard 232 (RS-232), and Plain Old Telephone Service (POTS).

According to an embodiment, the network 162 may be a communication network. The communication network may include at least one of a computer network, the Internet, the Internet of things, and a telephone network. According to an embodiment, a protocol (e.g., a transport layer protocol, data link layer protocol, or a physical layer protocol) for communication between the electronic device 100 and the external device may be supported by at least one of the applications 134, the application programming interface 133, the middleware 132, the kernel 131, and the communication interface 160.

The measurement module 170 may process at least some pieces of information acquired from other elements (e.g., the processor 120, the memory 130, the input/output interface 140, and the communication interface 160), and may provide the processed information to a user through various methods. For example, using the processor 120 or independently of the processor 120, the measurement module 170 may control at least some functions of the electronic device 100 such that the electronic device 100 synchronizes physical activity count values together with another electronic device (e.g., the electronic device 104). Additional information on the measurement module 170 may be provided through FIGS. 3 to 7.

Figure 3:
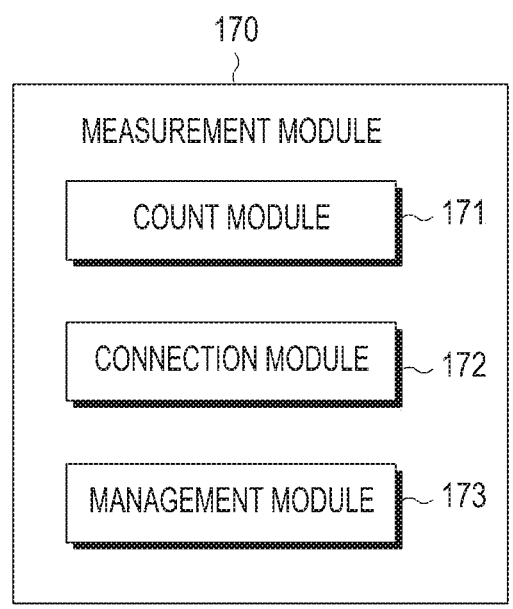
FIG. 3 is a block diagram illustrating a measurement module according to an embodiment of the present disclosure.

FIG. 3 is a block diagram illustrating a configuration of a measurement module of an electronic device (e.g., the electronic device 100) according to various embodiments of the present disclosure.

Referring to FIG. 3, a measurement module 170 may include a count module 171, a connection module 172, and a management module 173.

The count module 171 may count an amount of user physical activity, for example, the number of steps, using a sensor value input from the sensor 141 through the bus 110, and may store the number of counted steps in the memory 130.

The connection module 172 may make a control such that short range communication with an external device is connected, based on communication address information of the external device (e.g., the electronic device 104). A protocol of the short range communication may include one of, for example, WiFi, BT, and NFC. Furthermore, the short range communication may include at least one of, for example, a USB, a HDMI, RS-232, and POTS.

The management module 173 may allow count information including the start time and end time of a physical activity count and an amount of measured physical activity to be stored in the memory 130, according to a request for measuring the amount of physical activity and a request for stopping measuring of the amount of physical activity. For example, when a step count service is requested, the management module 173 may store the start time of the step count in the memory 130, and may control the count module 171 to start the step count. When a request for terminating the step count service is received or steps are not counted for a predetermined period of time, the management module 173 may store the count end time in the memory 130. The count start time, the count end time, and the number of counted steps may be stored as count information in the memory 130.

When short range communication with a sub-device having the function of measuring the amount of physical activity is connected by the connection module 172, the management module 173 may collect count information from the sub-device, and may determine an integrated measured quantity using the collected count information and the count information of the electronic device 100. The management module 173 may perform synchronization for the amount of physical activity by transferring, to the sub-device, the integrated measured quantity which has been determined. After the synchronization, the management module 173 may continue to count the amount of physical activity in conjunction with the sub-device.

For example, when short range communication with a sub-device having the step count function is connected by the connection module 172, the management module 173 may receive count information from the sub-device through the connection module 172. The management module 173 may determine the integrated number of steps using the count information of the electronic device 100 and the count information of the sub-device. The management module 173 may transmit the integrated number of steps to the sub-device through the connection module 172. The sub-device having received the integrated number of steps may change the number of steps thereof to the integrated number of steps, and may continue to count steps based on the integrated number of steps. Accordingly, step count synchronization may be made between the electronic device 100 and the sub-device.

According to embodiments, if the short range communication with the corresponding sub-device is maintained after the step count synchronization is completed, the management module 173 may stop counting the steps, receive a step count value from the sub-device, and renew the number of steps using the received step count value.

Furthermore, according to embodiments, if short range communication with a plurality of sub-devices is maintained after step count synchronization with the plurality of sub-devices is completed, the management module 173 may determine one of the plurality of sub-devices as an available sub-device, receive a step count value from the available sub-device, and renew the number of steps using the received step count value.

A case in which an amount of measured physical activity corresponds to the number of steps of a user will be described with reference to FIGS. 4 to 7.

First, a process of synchronizing a step count of an electronic device 100 will be described with reference to FIG. 4.

Figure 4:
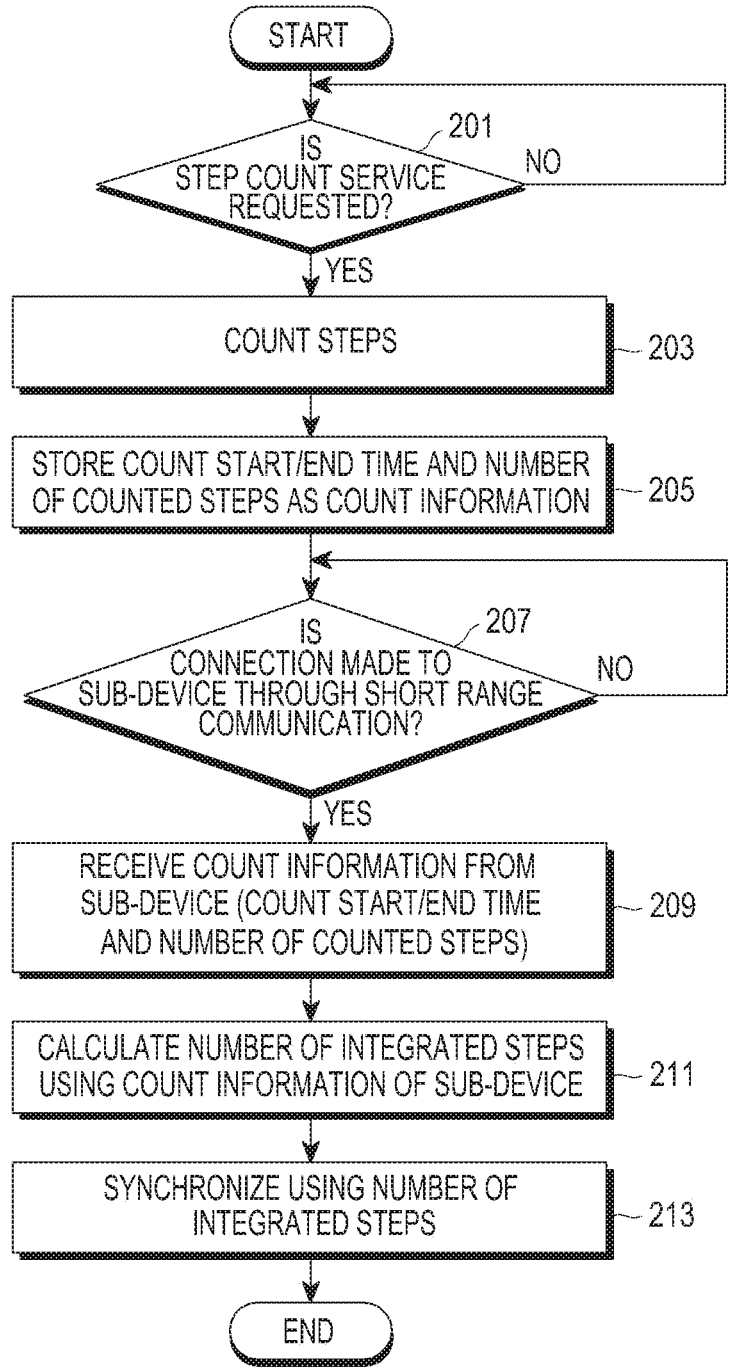
FIG. 4 is a flowchart illustrating an operation process of an electronic device according to various embodiments of the present disclosure.

FIG. 4 is a flowchart illustrating an operation process of an electronic device according to various embodiments of the present disclosure.

Referring to FIG. 4, a measurement module 170 of the electronic device 100 identifies whether a request for a step count service is received in operation 201, and when it is determined that the request has been received, the measurement module 170 may proceed to operation 203 to count steps. The measurement module 170 may store the count start time, the count end time, and the number of counted steps as count information in operation 205.

Meanwhile, when it is determined in operation 207 that the electronic device 100 has been connected with another electronic device having a step count function, namely, a sub-device through short range communication, the measurement module 170 may receive count information from the sub-device in operation 209. The measurement module 170 may request the count information from the sub-device, and the count information of the sub-device may be received in response to the request. Furthermore, after the sub-device is connected with the electronic device 100 through the short range communication, the sub-device may automatically transmit the count information to the electronic device 100.

The count information received from the sub-device may include the number of steps counted by the sub-device, and the count start information and count end information which are related to the number of counted steps.

The measurement module 170 may calculate the integrated number of steps using the count information of the electronic device 100, for example, first count information and the count information of the sub-device, for example, second count information, in operation 211. For example, the measurement module 170 may deduce a duration for which the step count has been repetitively performed, by comparing the count start time and the count end time included in the first count information with the count start time and the count end time included in the second count information. The measurement module 170 may determine the number of steps corresponding to the overlap duration for which the step count has been repetitively performed. The measurement module 170 may determine the integrated number of steps by subtracting the number of steps corresponding to the overlap duration from the sum of the steps counted by the respective devices. In another example, the measurement module 170 may determine which of the electronic device 100 and the sub-device has higher count reliability, and may also determine the integrated number of steps preferentially using the number of steps counted by the high reliability device.

Thereafter, the measurement module 170 may update the number of steps counted by the electronic device 100 using the integrated number of steps, and may transmit the integrated number of steps to the sub-device, thereby performing step count synchronization between the electronic device 100 and the sub-device in operation 213.

Such a synchronization process will be described below with reference to FIG. 5.

Figure 5:
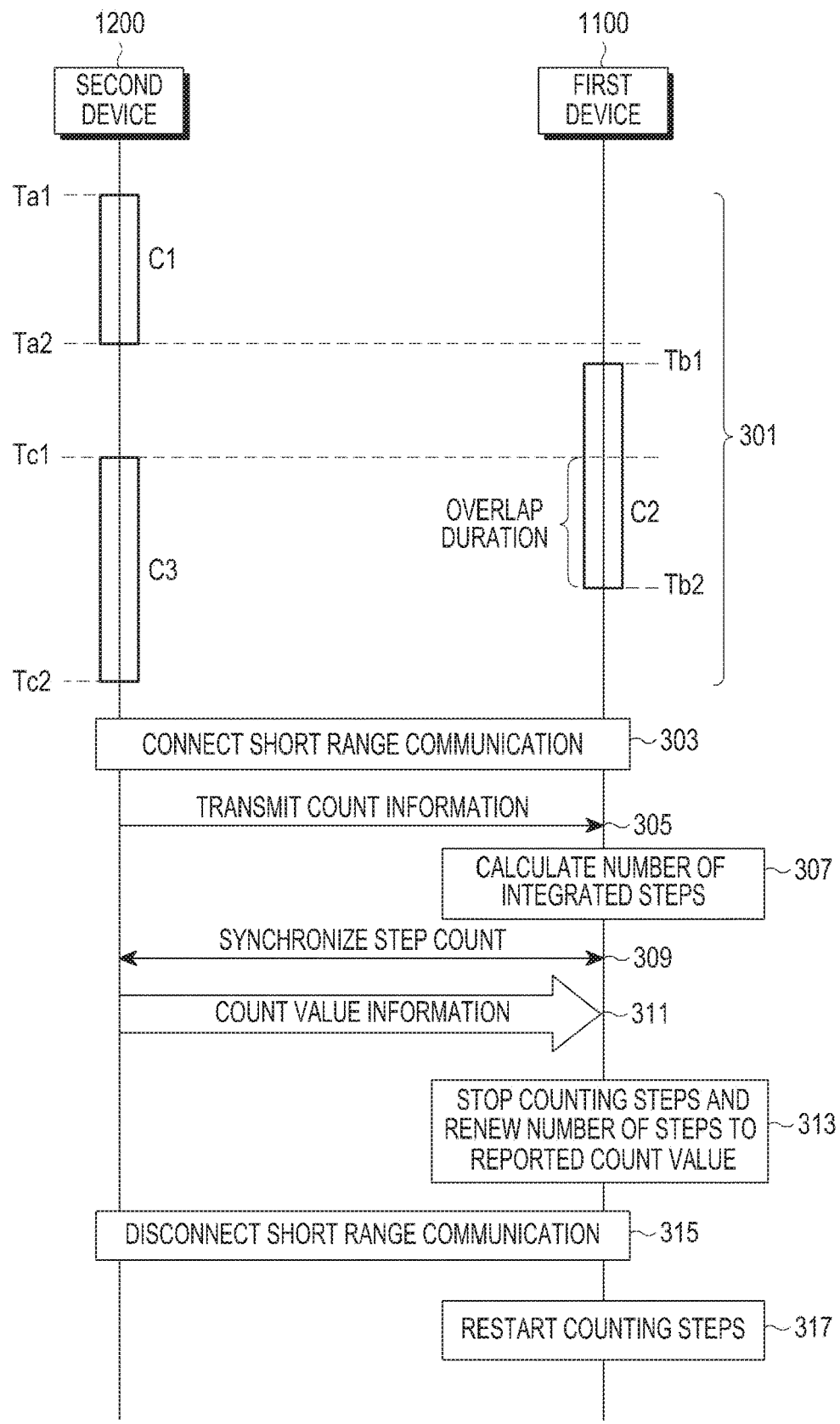
FIG. 5 illustrates an operation process of electronic devices according to an embodiment of the present disclosure.

FIG. 5 illustrates an operation process of two electronic devices having a step count function according to an embodiment of the present disclosure.

Referring to FIG. 5, it may be assumed that a first device 1100 (e.g., first device 100 shown in FIG. 2) is a main device and a second device 1200 is a sub-device. The first device 1100 may be one of, for example, a smart phone, a mobile phone, a video phone, an e-book reader, a laptop PC, a netbook computer, a PDA, a PMP, a digital audio player, a mobile medical instrument, a camera, and an electronic watch. The second device 1200 may be one of, for example, a step counter mounted to sports shoes, a wristband, glasses, or the like and an electronic watch.

Referring to FIG. 5, the two devices 1100 and 1200 may individually count steps without a communication connection in operation 301.

The second device 1200 has two count durations. The first count duration starts at Ta1 and ends at Ta2, and a step count value for the first count duration is C1. The second count duration starts at Tc1 and ends at Tc2, and a step count value for the second count duration is C3. Accordingly, the second device 1200 may store first count information including the start time Ta1, the end time Ta2, and the number of counted steps C1 in response to the first count duration and second count information including the start time Tc1, the end time Tc2, and the number of counted steps C3 in response to the second count duration.

In the case of the first device 1100, a count duration starts at Tb1 and ends at Tb2, and a step count value for the count duration is C2. Accordingly, the first device 1100 may store third count information including the start time Tb1, the end time Tb2, and the number of counted steps C2.

Thereafter, in operation 303, the first and second device 1100 and 1200 are connected with each other through short range communication, and in operation 305, the second device 1200 may transmit the count information, namely, the first count information and the second count information to the first device 1100.

A measurement module 170 of the first device 1100 may accordingly calculate the integrated number of steps using the first count information, the second count information, and the third count information.

For example, the measurement module 170 may detect an overlap duration for which the first and second devices 1100 and 1200 repetitively count steps, by comparing the start time and the end time included in the respective pieces of count information. The measurement module 170 may determine the number of steps corresponding to an overlap duration for which the steps have been repetitively counted. The number of steps corresponding to the overlap duration may be calculated by interpolating, extrapolating, or excluding the number of steps corresponding to the respective count durations including the overlap duration. The measurement module 170 may determine the integrated number of steps by subtracting the number of steps corresponding to the overlap duration from the sum of the steps counted by the respective devices.

The integrated number of steps may be obtained by Equation 1 applied to the embodiment illustrated in operation 301 of FIG. 5.

$$\text{Integrated number of Steps} = C1 + C2 + C3 - (C2\&C3) \qquad \text{Equation 1}$$

Here, $C2\&C3$ denotes the number of steps corresponding to the overlap duration.

According to another embodiment, the integrated number of steps may also be deduced depending on a priority of the devices. For example, when a smart phone and a smart watch are connected with each other, step detection of the smart watch worn on a user's body may be more reliable than that of the smart phone. In this case, if operations of the smart watch and the smart phone overlap each other in time, the number of steps counted by the smart watch may be unilaterally employed. In detection of human activity such as the step count, the smart watch secured to a specific region of the body may more accurately measure the value than the smart phone having a high degree of freedom for a device manipulation since it is easy to predict an operation of the smart watch. The integrated number of steps may be obtained by Equation 2 applied to the embodiment illustrated in operation 301 of FIG. 5. At this time, it is assumed that the second device 1200 has higher reliability than the first device 1100, that is, the priority of the second device is higher than that of the first device.

$$\text{Integrated number of Steps} = C1 + C3 + (C2\&C3^\wedge) \qquad \text{Equation 2}$$

Here, $C2\&C3^\wedge$ denotes a number obtained by subtracting the number of steps corresponding to the overlap duration from C2.

Referring back to FIG. 5, when the integrated number of steps is completely calculated in operation 307, the measurement module 170 of the first device 1100 may synchronize the step count of the first and second devices 1100 and 1200 using the integrated number of steps in operation 309.

Thereafter, the first and second devices may continue to count the steps based on the synchronized step count. Furthermore, according to embodiments, while the two devices are connected with each other through the short range communication, the number of steps counted by the two devices may be renewed using the number of steps counted by the device having high reliability for the step measurement.

For example, in a case where the first device 1100 is a smart phone and the second device 1200 is a smart watch, after the synchronization of the step count, only the second device 1200 may count steps, and the first device 1100 may be designated to suspend or stop counting steps. This is because the connection of the two devices implies that the two devices are within a predetermined distance and a user is more likely to simultaneously use the two devices. The device continuing to count the steps, namely, the second device 1200 may report the number of steps to the first device 1100, and the first device 1100 may accordingly renew the step count thereof using the reported number of steps. If the short range communication of one device is compulsorily terminated by the user, or the two devices are moved away from each other so that the communication is disconnected, the two devices may individually count the steps from that point on. In this case, the connection and disconnection time information of the short rang communication may be stored together. Operations 311 to 317 of FIG. 5 represent these operations.

In operation 311 of FIG. 5, the second device 1200 may transmit the number of counted steps to the first device 1100. Accordingly, in operation 313, the first device 1100 may stop counting the steps and may renew the number of steps thereof to the reported number of steps.

Thereafter, in operation 315, when the short range communication between the first and second devices 1100 and 1200 is disconnected, the first device 1100 may restart to count the steps. The first device 1100 may store the connection and disconnection time of the short range communication.

Next, with reference to FIGS. 6 and 7, an embodiment will be described below in which three or more electronic devices having a step count function are connected with each other through short range communication. In other words, the embodiment in which a plurality of sub-devices is connected to one main device will be described below.

Figure 6:
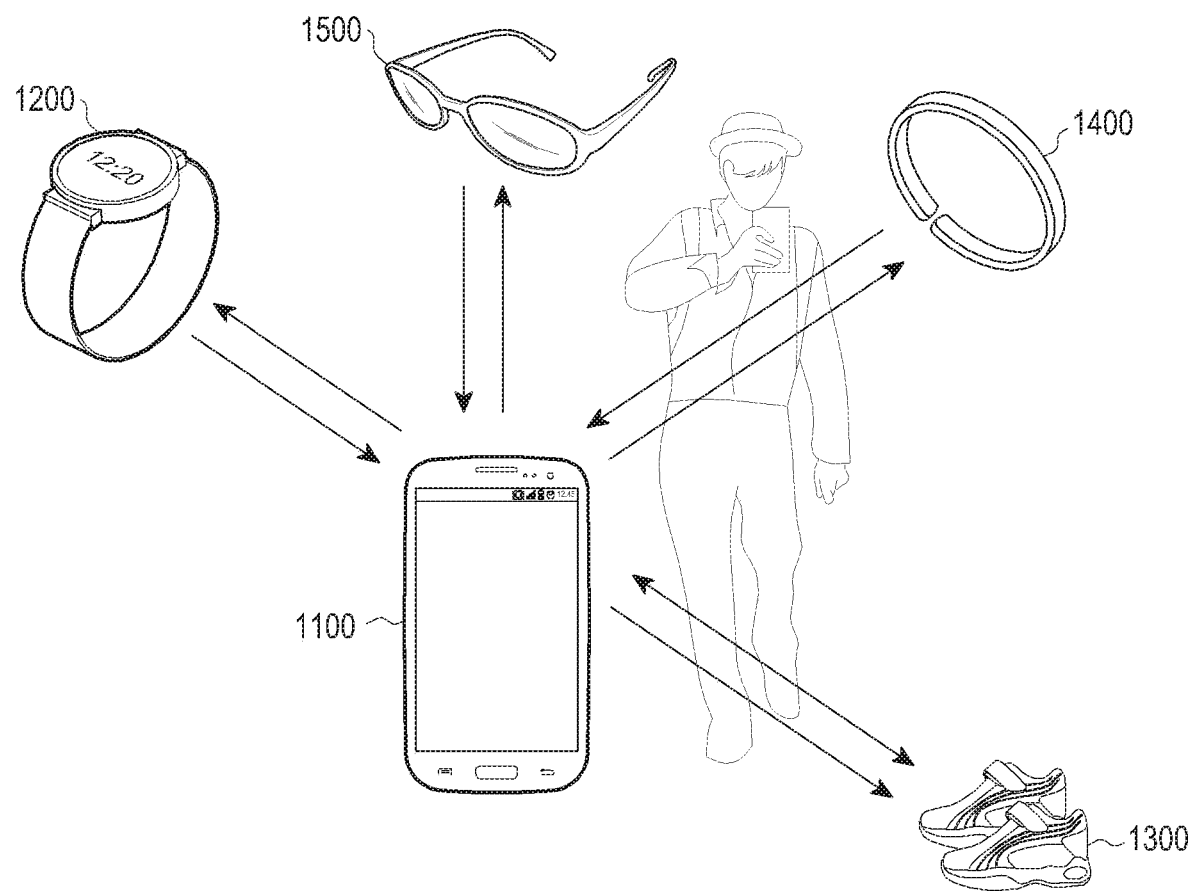
FIG. 6 illustrates a plurality of electronic devices interworked with each other according to an embodiment of the present disclosure.
Figure 7:
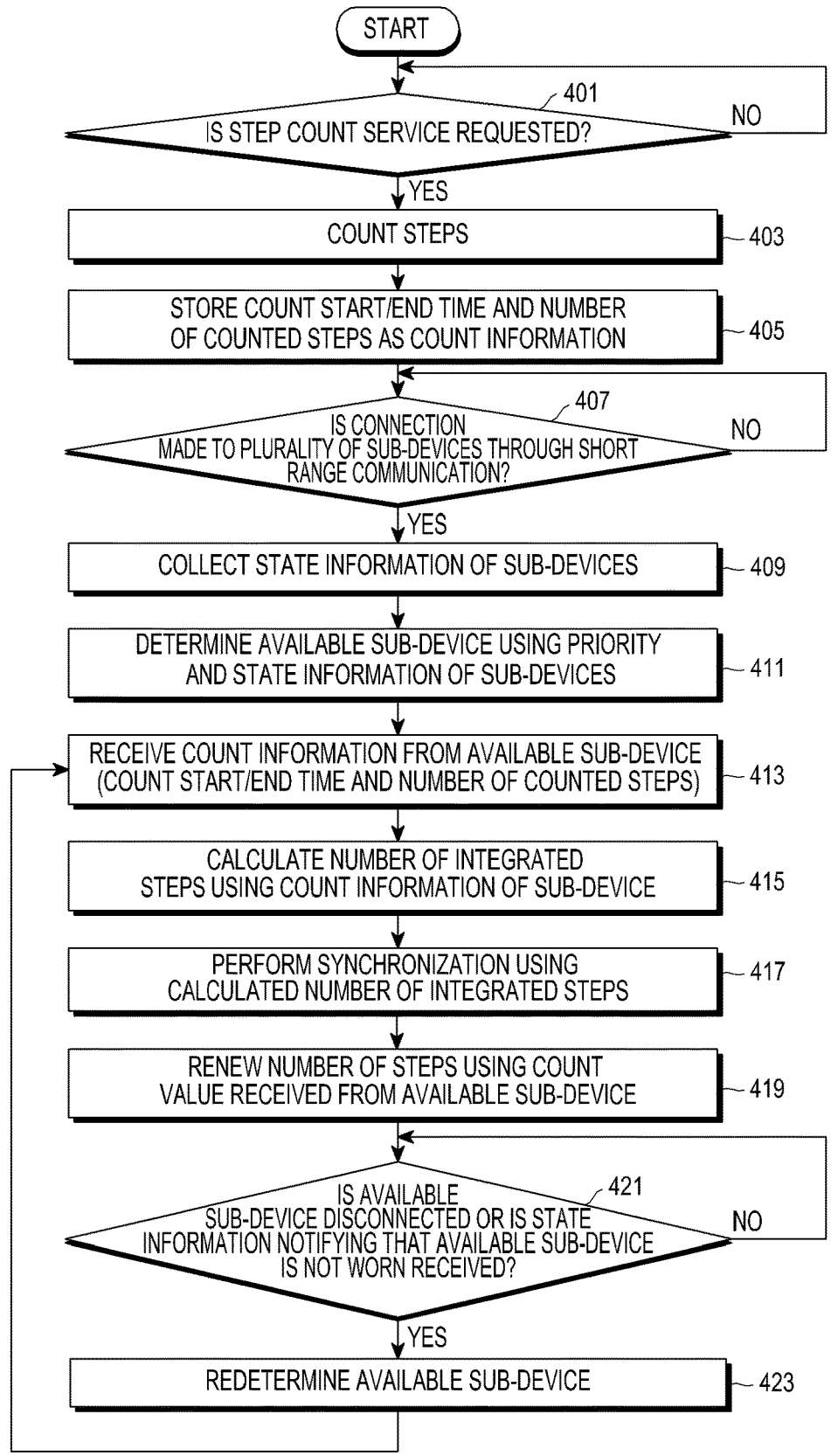
FIG. 7 is a flowchart illustrating an operation process of an electronic device according to another embodiment of the present disclosure.

FIG. 6 illustrates a plurality of electronic devices interworked with each other according to an embodiment of the present disclosure, and FIG. 7 is a flowchart illustrating an operation process of an electronic device according to the embodiment of FIG. 6.

Referring to FIG. 6, it is assumed that a user wears or carries all of a first device 1100, a second device 1200, a third device 1300, a fourth device 1400, and a fifth device 1500 on his/her body. Furthermore, it is assumed that each of the first device 1100, the second device 1200, the third device 1300, the fourth device 1400, and the fifth device 1500 has a step count function. The first device 1100 may be a smart phone, the second device 1200 may be a smart watch, the third device 1300 may be a step counter coupled to sports shoes, the fourth device 1400 may be a step counter coupled to a band, and the fifth device 1500 may be a step counter coupled to glasses. Furthermore, among the first device 1100, the second device 1200, the third device 1300, the fourth device 1400, and the fifth device 1500, the first device 1100 is assumed to be a main device, and the remaining devices are assumed to be sub-devices.

In a case of counting steps, among the smart phone 1100, the band 1400, the watch 1200, the sports shoes 1300, and the glasses 1500, the sports shoes 1300 may provide the most accurate value, and the band 1400, the watch 1200, the smart phone 1100 and the glasses 1500 may accurately count the steps in a serial order.

The sports shoes 1300 may detect accurate steps through a pressure sensor, and may easily calculate physical activity according to an activity pattern by accurately sensing jumping, running, and the like. The band 1400 may determine an action through an acceleration sensor while being worn on a wrist, a forearm, or the like. The watch 1200 may detect physical activity while being worn a wrist, and the glasses 1500 may detect physical activity while being worn on the head. The smart phone 1100 may detect physical activity while being located in a pocket or held with a hand.

A user may simultaneously wear the five devices on his body, or may carry them in three or two sets of devices. At this time, even though the user wears the devices through any type of configuration, the devices may individually count steps. If the devices are connected with each other through short range communication, synchronization of the physical activity may be performed, and a determination may be made as to whether count values measured by the respective devices are to be included and applied depending on a priority of the devices.

For example, when a user wears the band 1400 and the sports shoes 1300 at the same time, if the number of steps measured by the sports shoes 1300 is one hundred and the number of steps measured by the band 1400 is ninety eight, since the measured value through the sports shoes is determined to be more reliable than the measured value through the band, the integrated number of steps of the user may be determined as one hundred, and the measured value through the band 1400 may be corrected to one hundred.

In the embodiment of FIG. 6, when four accessories (the sports shoes 1300, the band 1400, the watch 1200, and the glasses 1500) are simultaneously connected with one smart phone 1100, only the number of steps counted by the highest priority device may be used depending on the priority of the devices. If the short range communication between the smart phone 1100 and the sports shoes 1300 having the highest priority is disconnected, the number of steps counted by the band 1400 having the next highest priority may be used.

In another embodiment, the priority may vary depending on a state in which the accessory devices are worn. For example, even though the sports shoes 1300, the band 1400, and the watch 1200 are connected with the smart phone 1100 through the short range communication, if a user takes off the sports shoes 1300 or does not wear the band 1400 and the watch 1200 on his/her body, the priority thereof may be made low, and the number of user's steps may be measured through the smart phone 1100. A contact sensor or heart rate sensor included in each device may determine whether the device is being worn on the user's body.

An example of the priority of the devices is illustrated in Table 1 below. The priority table may be stored in the memory 130.

TABLE 1

| Electronic device | Priority (The lower the number, the higher the priority) |
| --- | --- |
| Sports shoes (worn/not worn) | 0/999 |
| Band (worn/not worn) | 5/999 |
| Watch (worn/not worn) | 10/999 |
| Glasses (worn/not worn) | 50/999 |
| Smart phone (worn/not worn) | 15/30 |

FIG. 7 is a flowchart illustrating an operation process of a smart phone according to the embodiment of FIG. 6.

Referring to FIG. 7, a measurement module 170 of a smart phone 1100 identifies whether a request for a step count service is received in operation 401, and when it is determined that the request for the step count service has been received, the measurement module 170 may proceed to operation 403 to count steps. The measurement module 170 may store the count start time, the count end time, and the number of counted steps as count information in operation 405.

Meanwhile, when it is determined in operation 407 that the smart phone 1100 has been connected with a plurality of electronic devices each having a step count function, namely, the sub-devices (the sports shoes 1300, the band 1400, the watch 1200, and the glasses 1500) through short range communication, the measurement module 170 may collect state information from the sub-devices in operation 409. The state information may include information as to whether each sub-device is worn.

In operation 411, the measurement module 170 may determine the highest priority device as an available sub-device using the priority and the state information of the sub-devices. When all of the sports shoes 1300, the band 1400, the watch 1200, and the glasses 1500 are worn on a user's body, the sports shoes 1300 may be determined as the highest priority available sub-device. In operation 413, the measurement module 170 may receive count information from the highest priority available sub-device. The measurement module 170 may request the count information from the highest priority available sub-device, and the count information may be received in response to the request. The count information received from the highest priority available sub-device may include the number of steps counted by the highest priority available sub-device, and count start information and count end information which are related to the number of counted steps.

In operation 415, the measurement module 170 may calculate the integrated number of steps using the count information of the smart phone 1100, for example, first count information and the count information of the highest priority available sub-device, for example, second count information. In operation 417, the measurement module 170 may renew the number of steps counted by the smart phone 1100 using the integrated number of steps, and may transmit the integrated number of steps to all the connected sub-devices, namely, the sports shoes 1300, the band 1400, the watch 1200, and the glasses 1500, thereby performing synchronization of the step count between the smart phone 1100 and the sub-devices. The sports shoes 1300, the band 1400, the watch 1200, and the glasses 1500 which have received the integrated number of steps may change the number of accumulated steps thereof to the integrated number of steps, and may continue to count the steps.

After the synchronization of the step count is completed, the measurement module 170 may renew the number of steps using the count value received from the highest priority available sub-device in operation 419.

Meanwhile, when the connection of the highest priority available sub-device is terminated or state information notifying that the highest priority available sub-device is not worn is received in operation 421, the measurement module 170 may determine the highest priority available sub-device again in operation 423. Thereafter, the measurement module 170 may return to operation 413 to perform the above-described operations such as the synchronization of the step count.

In another embodiment, the priority of the devices may be configured based on accessibility according to a voice command. Most devices are provided with a microphone, and a user issues a command by making a sound with his/her voice, in which case the priority may be configured based on an order in which the voice command can be effectively input based on characteristics of the respective devices. For example, a headset worn on the user's ears is situated at a location where it may directly sense the voice. Accordingly, the headset has a higher weighted value for the voice sensing as compared with the glasses, the watch, the smart phone, and the like. If several devices capable of listening to a voice have to wait for a user's voice command, voice processing and the command may be performed based on the value of the headset among the received values of the several devices. Furthermore, without the several devices having to wait for the voice command at the same time, only the headset having the highest priority may receive the voice, and other devices may not perform an operation.

Figure 8:
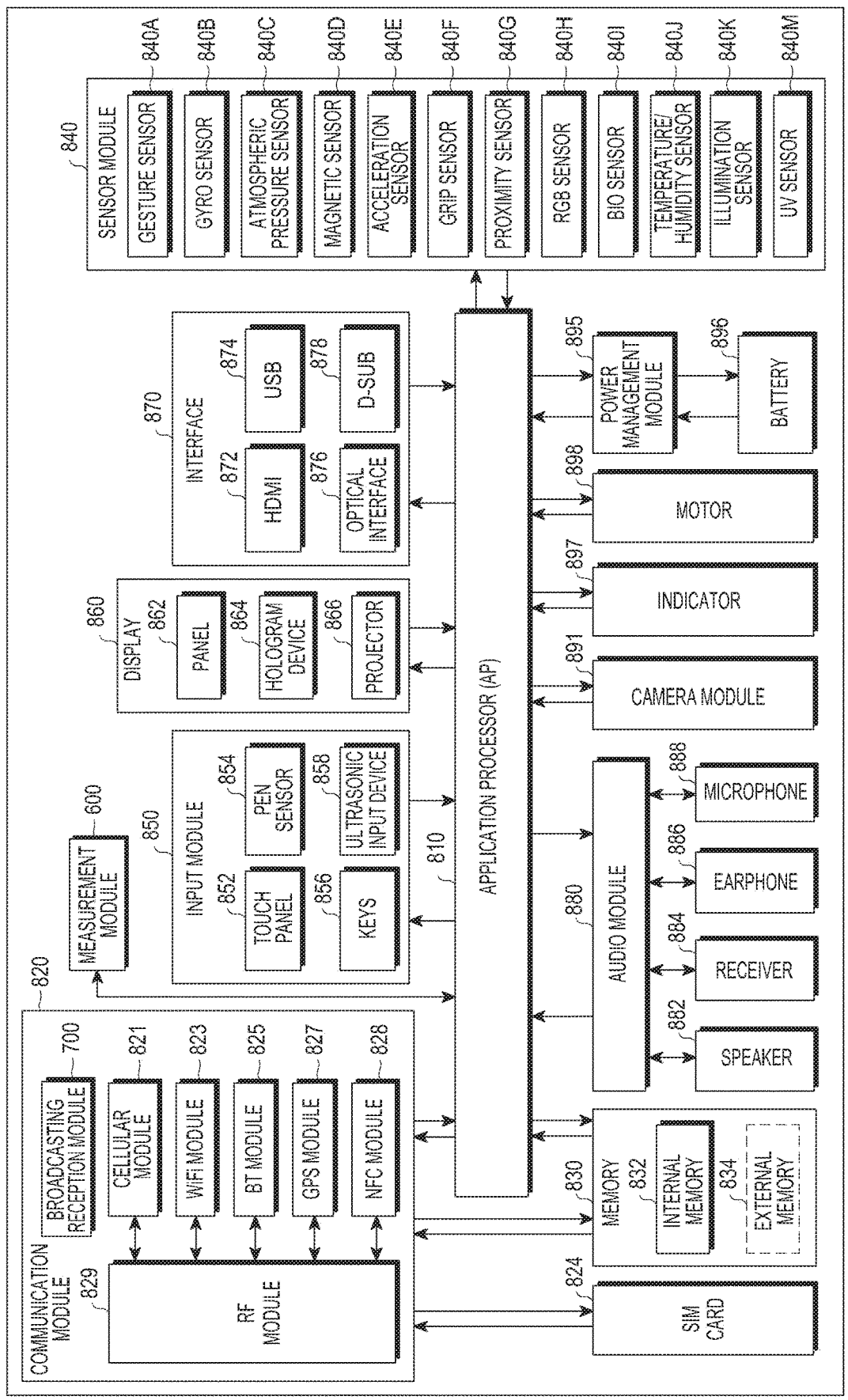
FIG. 8 is a block diagram of an electronic device for which physical activity measurement according to various embodiments of the present disclosure is employed.

FIG. 8 is a block diagram of an electronic device according to various embodiments of the present disclosure.

An electronic device 801 may include all or some of the electronic devices 10 and 20 illustrated in FIG. 1.

Referring to FIG. 8, the electronic device 801 may include a measurement module 600, at least one Application Processor (AP) 810, a communication module 820, a Subscriber Identifier Module (SIM) card 824, a memory 830, a sensor module 840, an input module 850, a display 860, an interface 870, an audio module 880, a camera module 891, a power management module 895, a battery 896, an indicator 897, and a motor 898.

The AP 810 may control a plurality of hardware or software components connected to the AP 810 by driving an operating system or an application program, process various data including multimedia data, and perform calculations. The AP 810 may be implemented by, for example, a System on Chip (SoC). According to an embodiment, the AP 810 may further include a Graphic Processing Unit (GPU).

The communication module 820 may include the communication interface 160 and may perform data transmission/reception in communication between the electronic device 800 which may include the electronic device 101 and other electronic devices (e.g., the electronic device 104 and the server 106) connected thereto through a network. According to an embodiment, the communication module 820 may include a broadcasting reception module 700, a cellular module 821, a WiFi module 823, a BT module 825, a GPS module 827, an NFC module 828, and a Radio Frequency (RF) module 829.

The cellular module 821 may provide a voice, a call, a video call, an SMS, or an Internet service through a communication network (for example, LTE, LTE-A, CDMA, WCDMA, UMTS, WiBro, or GSM). Furthermore, the cellular module 821 may distinguish and authenticate electronic devices within a communication network, for example, using a subscriber identification module (e.g., the SIM card 824). According to an embodiment, the cellular module 821 may perform at least some of the functions which can be provided by the AP 810. For example, the cellular module 821 may perform at least some of the multimedia control functions.

According to an embodiment, the cellular module 821 may include a Communication Processor (CP) (not shown). Furthermore, the cellular module 821 may be implemented by, for example, an SoC. Although the components such as the cellular module 821 (for example, the CP), the memory 830, and the power management module 895 are illustrated as separate components from the AP 810 in FIG. 8, the AP 810 may include at least some of the above described components (for example, cellular module 821) in an embodiment.

According to an embodiment, the AP 810 or the cellular module 821 (for example, the CP) may load a command or data received from at least one of a non-volatile memory and other component elements connected thereto to a volatile memory and process the loaded command or data. Furthermore, the AP 810 or the cellular module 821 may store data received from or generated by at least one of other components in a non-volatile memory.

The WiFi module 823, the BT module 825, the GPS module 827, and the NFC module 828 may include, for example, a processor for processing data transmitted/received through the corresponding module. Although the cellular module 821, the WiFi module 823, the BT module 825, the GPS module 827, and the NFC module 828 are illustrated as separate blocks in FIG. 8, at least some (for example, two or more) of the cellular module 821, the WiFi module 823, the BT module 825, the GPS module 827, and the NFC module 828 may be included in one Integrated Circuit (IC) or one IC package in one embodiment. For example, at least some (e.g., a communication processor corresponding to the cellular module 821 and a WiFi processor corresponding to the WiFi module 823) of processors corresponding to the cellular module 821, the WiFi module 823, the BT module 825, the GPS module 827, and the NFC module 828, respectively, may be implemented as one SoC.

The RF module 829 may transmit/receive data, for example, an RF signal. Although not illustrated, the RF unit 829 may include, for example, a transceiver, a Power Amp Module (PAM), a frequency filter, a Low Noise Amplifier (LNA), or the like. Furthermore, the RF module 829 may further include a component, such as a conductor or a conducting wire, for transmitting/receiving electronic waves over a free air space in wireless communication. Although the cellular module 821, the WiFi module 823, the BT module 825, the GPS module 827, and the NFC module 828 share one RF module 829 in FIG. 8, at least one of the cellular module 821, the WiFi module 823, the BT module 825, the GPS module 827, and the NFC module 828 may transmit/receive an RF signal through a separate RF module in one embodiment.

The SIM card 824 may be a card including a subscriber identification module, and may be inserted into a slot formed in a particular portion of the electronic device. The SIM card 824 may include unique identification information (for example, an Integrated Circuit Card IDentifier (ICCID)) or subscriber information (for example, International Mobile Subscriber Identity (IMSI)).

The memory 830 may include the memory 130 may include an internal memory 832 or an external memory 834. The internal memory 832 may include, for example, at least one of a volatile memory (for example, a Dynamic Random Access Memory (RAM) (DRAM), a Static RAM (SRAM), a Synchronous DRAM (SDRAM), and the like), and a non-volatile memory (for example, One Time Programmable Read-Only Memory (OTPROM), a Programmable ROM (PROM), an Erasable and Programmable ROM (EPROM), an Electrically Erasable and Programmable ROM (EEPROM), a mask ROM, a flash ROM, a NAND flash memory, a NOR flash memory, and the like).

According to an embodiment, the internal memory 832 may be a Solid State Drive (SSD). The external memory 834 may further include a flash drive, for example, a Compact Flash (CF), a Secure Digital (SD), a Micro Secure Digital (Micro-SD), a Mini Secure Digital (Mini-SD), an extreme Digital (xD), a memory stick, or the like. The external memory 834 may be functionally connected to the electronic device 801 through various interfaces. According to an embodiment, the electronic device 801 may further include a storage device (or storage medium) such as a hard drive.

The sensor module 840 may measure a physical quantity or detect an operation state of the electronic device 801, and may convert the measured or detected information to an electronic signal. The sensor module 840 may include at least one of, for example, a gesture sensor 840A, a gyro sensor 840B, an atmospheric pressure sensor 840C, a magnetic sensor 840D, an acceleration sensor 840E, a grip sensor 840F, a proximity sensor 840G a color sensor 840H (e.g., a Red/Green/Blue (RGB) sensor), a bio-sensor 840I, a temperature/humidity sensor 840J, an illumination sensor 840K, and an Ultra Violet (UV) sensor 840M. Additionally or alternatively, the sensor module 840 may include (not shown), for example, a E-nose sensor, an ElectroMyoGraphy (EMG) sensor, an ElectroEncephaloGram (EEG) sensor, an ElectroCardioGram (ECG) sensor, an InfraRed (IR) sensor, an iris sensor, a fingerprint sensor, and the like. The sensor module 840 may further include a control circuit for controlling one or more sensors included therein.

The input device 850 may include a touch panel 852, a (digital) pen sensor 854, a key 856, or an ultrasonic input device 858. The touch panel 852 may recognize a touch input through at least one of a capacitive type, a resistive type, an infrared type, and an acoustic wave type. The touch panel 852 may further include a control circuit. The capacitive type touch panel may recognize physical contact or proximity. The touch panel 852 may further include a tactile layer. In this case, the touch panel 852 may provide a tactile reaction to the user.

The (digital) pen sensor 854 may be implemented, for example, using a method identical or similar to a method of receiving a touch input of the user, or using a separate recognition sheet. The key 856 may include, for example, a physical button, an optical key, or a keypad. The ultrasonic input device 858 may identify data by detecting an acoustic wave using a microphone (for example, microphone 888) of the electronic device 801 through an input unit generating an ultrasonic signal, and may perform wireless recognition. According to an embodiment, the electronic device 801 may receive a user input from an external device (for example, computer or server) connected thereto using the communication module 820.

The display 860 may include display 150 and may include a panel 862, a hologram device 864, or a projector 866. The panel 862 may be, for example, a Liquid Crystal Display (LCD) or an Active Matrix Organic Light Emitting Diode (AM-OLED). The panel 862 may be implemented to be, for example, flexible, transparent, or wearable. The panel 862 may be configured by the touch panel 852 and one module. The hologram 864 may show a stereoscopic image in the air using interference of light. The projector 866 may project light on a screen to display an image. The screen may be located, for example, inside or outside the electronic device 801. According to an embodiment, the display 860 may further include a control circuit for controlling the panel 862, the hologram device 864, or the projector 866.

The interface 870 may include, for example, an HDMI 872, a USB 874, an optical interface 876, or a D-subminiature (D-sub) 878. The interface 870 may be included in, for example, the communication interface 160 illustrated in FIG. 1. Additionally or alternatively, the interface 290 may include, for example, a Mobile High-definition Link (MHL) interface, a Secure Digital (SD)/Multi-Media Card (MMC) interface, or an Infrared Data Association (IrDA) standard interface.

The audio module 880 may bilaterally convert a sound and an electronic signal. At least some elements of the audio module 880 may be included in, for example, the input/output interface 140 illustrated in FIG. 2. The audio module 880 may process sound information input or output through, for example, a speaker 882, a receiver 884, earphones 886, the microphone 888, and the like.

The camera module 891 is a device for capturing a still image or a video, and, according to an embodiment, may include one or more image sensors (for example, a front side sensor or a back side sensor), a lens, an Image Signal Processor (ISP) (not illustrated), or a flash (not illustrated) (for example, an LED or xenon lamp).

The power management module 895 may manage power of the electronic device 801. Although not illustrated, the power management module 895 may include, for example, a Power Management Integrated Circuit (PMIC), a charger IC, or a battery or fuel gauge.

The PMIC may be mounted in, for example, an integrated circuit or an SoC semiconductor. Charging methods may be classified into a wired charging method and a wireless charging method. The charger IC may charge a battery and prevent over voltage or over current from being introduced from a charger. According to an embodiment, the charger IC may include a charger IC for at least one of the wired charging method and the wireless charging method. A magnetic resonance scheme, a magnetic induction scheme, or an electromagnetic scheme can be exemplified as the wireless charging method, and an additional circuit for wireless charging, such as a coil loop circuit, a resonance circuit, a rectifier circuit, and the like may be added.

The battery gauge may measure, for example, a remaining quantity of the battery 896, or a voltage, a current, or a temperature during the charging. The battery 896 may store or generate electricity, and may supply power to the electronic device 801 using the stored or generated electricity. The battery 896 may include, for example, a rechargeable battery or a solar battery.

The indicator 897 may display a specific status of the electronic device 801 or a part (for example, the AP 810) of electronic device, for example, a booting status, a message status, a charging status, and the like. The motor 898 may convert an electrical signal to a mechanical vibration. Although not illustrated, the electronic device 801 may include a processing unit (for example, GPU) for supporting a mobile TV. The processing unit for supporting the mobile TV may process, for example, media data according to a standard of Digital Multimedia Broadcasting (DMB), Digital Video Broadcasting (DVB), media flow or the like.

The described component elements of an electronic device according to various embodiments of the present disclosure may be formed of one or more components, and a name of a corresponding component element may be changed based on a type of electronic device. An electronic device according to various embodiments of the present disclosure may be formed to include at least one of the described component elements, and a few component elements may be omitted or additional component elements may be further included. Also, a few of component elements of an electronic device according to various embodiments of the present disclosure are coupled to form a single entity, and may equivalently execute functions of the corresponding component elements which are not coupled.

The "module" used in various embodiments of the present disclosure may refer to, for example, a "unit" including one of hardware, software, and firmware, or a combination of two or more of the hardware, software, and firmware. The "module" may be interchangeable with a term, such as a unit, a logic, a logical block, a component, or a circuit. The "module" may be a minimum unit of an integrated component element or a part thereof. The "module" may be a minimum unit for performing one or more functions or a part thereof. The "module" may be mechanically or electronically implemented. For example, the "module" according to various embodiments of the present disclosure may include at least one of an Application-Specific Integrated Circuit (ASIC) chip, a Field-Programmable Gate Arrays (FPGAs), and a programmable-logic device for performing operations which have been known or are to be developed hereafter.

According to various embodiments, at least part of a device (for example, modules or functions thereof) or a method (for example, operations) according to the various embodiments of the present disclosure may be embodied by, for example, an instruction stored in a computer readable storage medium provided in a form of a programming module. When the command is executed by one or more processors (for example, processor 120), the one or more processors may perform a function corresponding to the command. The computer-readable storage medium may be, for example, the memory 130. At least a part of the programming module may be implemented (for example, executed) by, for example, the processor 120. At least a part of the programming module may include, for example, a module, a program, a routine, a set of instructions and/or a process for performing one or more functions.

The computer-readable recording medium may include magnetic media such as a hard disk, a floppy disk, and a magnetic tape, optical media such as a Compact Disc Read Only Memory (CD-ROM) and a Digital Versatile Disc (DVD), magneto-optical media such as a floptical disk, and hardware devices specially configured to store and perform a program instruction (for example, programming module), such as a ROM, a Random Access Memory (RAM), a flash memory and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

A module, a programming module according to various embodiments the present disclosure may include at least one of the described component elements, a few of the component elements may be omitted, or additional component elements may be included. Operations executed by a module, a programming module, or other component elements according to various embodiments of the present disclosure may be executed sequentially, in parallel, repeatedly, or in a heuristic manner. Also, a few operations may be executed based on a different order, may be omitted, or may additionally include another operation.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method of measuring physical activity of a user by a mobile electronic device, the method comprising:
   sensing by the mobile electronic device, an amount of physical activity of the user;

determining, by the mobile electronic device, first count information based on the sensed physical activity of the user, the first count information comprising:
a first count start time,
a first count end time, and
a first amount of the physical activity counted between the first count start time and the first count end time;
receiving, by the mobile electronic device, second count information based on the physical activity of the user, the second count information comprising:
a second count start time,
a second count end time, and
a second amount of the physical activity counted between the second count start time and the second count end time, the second amount of the physical activity determined by an entity different from the mobile electronic device;
determining a priority between the mobile electronic device and the entity;
determining an integrated amount of the physical activity; and
synchronizing first amount of the physical activity based on the first count information and second amount of the physical activity based on the second count information according to the determined priority,
wherein the amount of physical activity is counted by the mobile electronic device or the entity having a higher priority determined based on the determined priority of the mobile electronic device and the entity using weighted value based on a user input.

2. The method of claim 1, wherein the priority assigned to the mobile electronic device and the entity is set based on a user input.

3. The method of claim 2, wherein the user input is entered by an input interface which transfers instructions or data from a user.

4. The method of claim 3, wherein the priority of the mobile electronic device and the entity is configured based on accessibility according to a command of the user or by the mobile electronic device.

5. The method of claim 1, wherein the entity comprises at least one other device connected with the mobile electronic device through short range communication.

6. A mobile electronic device comprising:
a sensor;
a transceiver; and
a controller configured to:
sense, using the sensor, an amount of a physical activity of a user,
determine, by the mobile electronic device, first count information based on the sensed physical activity of the user, the first count information comprising:
a first count start time,
a first count end time, and
a first amount of the physical activity counted between the first count start time and the first count end time,
control the transceiver to receive second count information based on the physical activity of the user, the second count information comprising:
a second count start time,
a second count end time, and
a second amount of the physical activity counted between the second count start time and the second count end time, the second amount of the physical activity determined by an entity different from the mobile electronic device,
determine a priority between the mobile electronic device and the entity,
determine an integrated amount of the physical activity; and
synchronize first amount of the physical activity based on the first count information and second amount of the physical activity based on the second count information according to the determined priority,
wherein the integrated amount of the physical activity is counted by the mobile electronic device or the entity having a higher priority determined based on the determined priority of the mobile electronic device and the entity using weighted value based on a user input.

7. The mobile electronic device of claim 6, wherein the priority assigned to the mobile electronic device and the entity is set based on a user input.

8. The mobile electronic device of claim 7, wherein the user input is entered by an input interface which transfers instructions or data from a user.

9. The mobile electronic device of claim 8, wherein the priority of the mobile electronic device and the entity is configured based on accessibility according to a command of the user or the controller.

10. The mobile electronic device of claim 6, wherein the entity comprises at least one other device connected with the mobile electronic device through short range communication.

11. An operating method of an electronic device, the method comprising:
establishing, by using a communication circuit, a short range communication connection with an external device;
determining a priority between the electronic device and the external device;
based on the establishing of the short range communication connection with the external device, comparing a priority for the electronic device with a priority for the external device; and
in response to a request for providing an amount of physical activity:
based on the priority for the electronic device being higher than the priority for the external device, providing a first amount of the physical activity which is acquired by using a sensor in the electronic device, the first amount of the physical activity being associated with a movement of the electronic device,
based on the priority for the external device being higher than the priority for the electronic device, providing a second amount of the physical activity which is acquired by the external device and transmitted from the external device to the electronic device through the established short range communication connection, the second amount of the physical activity being associated with a movement of the external device,
releasing, by using the communication circuit, the short range communication connection with the external device while one of the first amount of the physical activity or the second amount of the physical activity is provided according to a comparison between the priority for the electronic device being higher and the priority for the external device, in response to the short range communication connection with the external device being released, providing a third amount of the physical activity which is acquired by using the sensor in the electronic device, and
determining an integrated amount of physical activity counted by the electronic device or the external device having a higher priority determined based on the priority of the electronic device and the external device using weighted value based on a user input.

12. The method of claim 11, wherein the priority of the electronic device and the priority of the external device are set based on a user input.

13. An electronic device comprising:
a sensor;
a communication circuit; and
a controller configured to:
establish, by using the communication circuit, a short range communication connection with an external device,
based on establishing the short range communication connection with the external device, determine a priority between the electronic device and the external device, and compare a priority among the electronic device and the external device, and
in response to a request for providing an amount of physical activity:
based on the priority for the electronic device being higher than the priority for the external device, provide a first amount of the physical activity which is acquired by using a sensor in the electronic device, the first amount of the physical activity being associated with a movement of the electronic device,
based on the priority for the external device being higher than the priority for the electronic device, provide a second amount of the physical activity which is acquired by the external device and transmitted from the external device to the electronic device through the established communication connection, the second amount of the physical activity being associated with a movement of the external device,
release, by using the communication circuit, the short range communication connection with the external device while one of the first amount of the physical activity or the second amount of the physical activity is provided according to a comparison between the priority for the electronic device being higher and the priority for the external device, in response to the short range communication connection with the external device being released, provide a third amount of the physical activity which is acquired by using the sensor in the electronic device, and
determine an integrated amount of the physical activity counted by the electronic device or the external device having a higher priority determined based on the priority of the electronic device and the external device using weighted value based on a user input.

14. The electronic device of claim 13, wherein the priority of the electronic device and the priority of the external device are set based on a user input.

* * * * *